United States Patent
Kwong et al.

(10) Patent No.: US 11,686,013 B2
(45) Date of Patent: Jun. 27, 2023

(54) METHODS OF SCREENING ANTIGEN-BINDING MOLECULES BY NORMALIZING FOR THE CONCENTRATION OF ANTIGEN-BINDING MOLECULE

(71) Applicant: Meso Scale Technologies, LLC., Rockville, MD (US)

(72) Inventors: Ka Y. Kwong, Gaithersburg, MD (US); Ilia V. Davydov, Rockville, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 398 days.

(21) Appl. No.: 16/971,752

(22) PCT Filed: Feb. 22, 2019

(86) PCT No.: PCT/US2019/019290
§ 371 (c)(1),
(2) Date: Aug. 21, 2020

(87) PCT Pub. No.: WO2019/165304
PCT Pub. Date: Aug. 29, 2019

(65) Prior Publication Data
US 2021/0087709 A1    Mar. 25, 2021

Related U.S. Application Data

(60) Provisional application No. 62/634,556, filed on Feb. 23, 2018.

(51) Int. Cl.
*C40B 30/04* (2006.01)
*C07K 16/00* (2006.01)
*C07K 16/26* (2006.01)
*C12N 15/10* (2006.01)

(52) U.S. Cl.
CPC ............ *C40B 30/04* (2013.01); *C07K 16/005* (2013.01); *C07K 16/26* (2013.01); *C12N 15/1037* (2013.01)

(58) Field of Classification Search
None
See application file for complete search history.

(56) References Cited

U.S. PATENT DOCUMENTS

| 4,683,195 A | 7/1987 | Mullis et al. |
| 5,091,513 A | 2/1992 | Huston et al. |
| 5,093,268 A | 3/1992 | Leventis et al. |
| 5,147,806 A | 9/1992 | Kamin et al. |

(Continued)

FOREIGN PATENT DOCUMENTS

| WO | 98/12539 A1 | 9/1997 |
| WO | 97/36931 A1 | 10/1997 |

(Continued)

OTHER PUBLICATIONS

Chothia et al., "Canonical structures for the hypervariable regions of immunoglobulins," J. Mol. Biol. 196:901-917 (1987).

(Continued)

*Primary Examiner* — Christian C Boesen
(74) *Attorney, Agent, or Firm* — Medler Ferro Woodhouse & Mills (57) ABSTRACT

The invention provides singleplex and multiplex assays for screening of antigen-binding molecules for their affinity to antigens by normalizing for the concentration of the antigen-binding molecule.

23 Claims, 2 Drawing Sheets

Spot A1     Spot B2

(56) References Cited

U.S. PATENT DOCUMENTS

| | | |
|---|---|---|
| 5,238,808 A | 8/1993 | Bard et al. |
| 5,240,863 A | 8/1993 | Shibue et al. |
| 5,308,754 A | 5/1994 | Kankare et al. |
| 5,324,457 A | 6/1994 | Zhang et al. |
| 5,589,136 A | 12/1996 | Northrup et al. |
| 5,591,581 A | 1/1997 | Massey et al. |
| 5,597,910 A | 1/1997 | Gudibande et al. |
| 5,641,623 A | 6/1997 | Martin |
| 5,643,713 A | 7/1997 | Liang et al. |
| 5,679,519 A | 10/1997 | Oprandy |
| 5,705,402 A | 1/1998 | Leland et al. |
| 5,731,147 A | 3/1998 | Bard et al. |
| 5,776,672 A | 7/1998 | Hashimoto et al. |
| 5,786,141 A | 7/1998 | Bard et al. |
| 5,846,485 A | 12/1998 | Leland et al. |
| 5,866,434 A | 2/1999 | Massey et al. |
| 5,892,019 A | 4/1999 | Schlom et al. |
| 5,939,598 A | 8/1999 | Kucherlapati et al. |
| 6,066,448 A | 5/2000 | Wohlstadter et al. |
| 6,136,268 A | 10/2000 | Ala-Kleme et al. |
| 6,207,369 B1 | 3/2001 | Wohlstadter et al. |
| 6,214,552 B1 | 4/2001 | Heroux et al. |
| 6,881,557 B2 | 4/2005 | Foote |
| 6,939,720 B2 | 9/2005 | Chandler et al. |
| 6,977,722 B2 | 12/2005 | Wohlstadter et al. |
| 7,842,246 B2 | 11/2010 | Wohlstadter et al. |
| 2005/0214860 A1 | 9/2005 | Zhu et al. |
| 2006/0148100 A1 | 7/2006 | Madison et al. |
| 2013/0338017 A1 | 12/2013 | Dubridge et al. |
| 2016/0069872 A1 | 3/2016 | Glezer et al. |

FOREIGN PATENT DOCUMENTS

| | | |
|---|---|---|
| WO | 98/52041 A1 | 11/1998 |
| WO | 98/57154 A1 | 12/1998 |
| WO | 99/14599 A1 | 3/1999 |
| WO | 99/63347 A2 | 5/1999 |
| WO | 99/32662 A1 | 7/1999 |
| WO | 99/58962 A1 | 11/1999 |
| WO | 00/03233 A3 | 1/2000 |
| WO | 2010040073 A1 | 4/2010 |

OTHER PUBLICATIONS

Hamers-Casterman et al., "Naturally occurring antibodies devoid of light chains," Nature 363:446-448 (1993).

Hu et al., "Minibody: A novel engineered anti-carcinoembryonic antigen antibody fragment (single-chain Fv-CH3) which exhibits rapid, high-level targeting of xenografts," Cancer Res. 56(13):3055-61 (1996).

Kunik et al., "Paratome: An online tool for systematic identification of antigen-binding regions in antibodies based on sequence or structure," Nucl. Acids Res. 40:W521-W524 (2012).

Murali et al., "Antibody like peptidomimetics as large scale immunodetection probes," Cell Mol. Biol. (Noisy-le-grand) 49(2):209-16 (2003).

Roux et al., "Comparisons of the Ability of Human IgG3 Hinge Mutants, IgM, IgE, and IgA2, to Form Small Immune Complexes: A Role for Flexibility and Geometry," J. Immunol. 161:4083 (1998).

International Search Report dated Jul. 12, 2019 in International Application No. PCT/US2019/019290.

METHODS OF SCREENING ANTIGEN-BINDING MOLECULES BY NORMALIZING FOR THE CONCENTRATION OF ANTIGEN-BINDING MOLECULE

BACKGROUND OF THE INVENTION

Field of the Invention

The present invention relates to methods of conducting binding assays in singleplex and multiplex formats.

Description of Related Art

Biomarker assays typically require availability of diverse antibodies that can recognize multiple epitopes on an antigen. Hybridoma development and phage display are two well-known techniques to develop such diverse antibodies. Hybridomas are used to produce monoclonal antibodies that are then screened for their binding affinity to an antigen. Screening of hybridoma clones during monoclonal antibody development involves testing of large numbers of cell culture supernatants over a short period typically using an indirect ELISA assay. This process is labor intensive, and usually it is difficult to perform several screening techniques in parallel or select antibodies with different specificities during screening.

Phage display is also a powerful technology employed in the development of therapeutic antibodies. Phage display libraries can be used for selection of fully human antibodies, for humanization of antibodies from non-human origin and for selection of antibody mutants with increased affinity. One of the challenges in this technology is the ability to quickly identify desirable phage clones in a pool of phages selected after bio-panning. Typically, individual phage colonies from the output pool are picked and their binding activity is confirmed by a colorimetric ELISA assay. The narrow dynamic range of colorimetric ELISA (less than 2 orders of magnitude) and the large variation in the display level of antibodies on individual phage clones limit the utility of this type of primary screening to selecting candidate clones for extensive follow up analysis. Subsequent antigen titration experiments or high throughput $K_D$ measurements are often required to select the phage clones with desired characteristics after the initial screening.

SUMMARY OF THE INVENTION

In embodiments, the invention provides methods of screening a candidate antigen-binding molecule for affinity to an antigen, comprising: (a) contacting the candidate antigen-binding molecule with a substrate, the substrate comprising (i) an antigen immobilized on the substrate, and (ii) a normalization binding molecule immobilized on the substrate; (b) detecting a binding of the candidate antigen-binding molecule with the antigen on the substrate; (c) detecting a binding of the candidate antigen-binding molecule from (b) to the immobilized normalization binding molecule to determine a concentration of the candidate antigen-binding molecule; and (d) determining the affinity of the candidate antigen-binding molecule from the binding of the candidate antigen molecule determined in (b) and the binding of the antigen-binding molecule to the normalization binding molecule determined in (c).

In aspects of the invention, the candidate antigen-binding molecule is selected from the group consisting of an immunoglobulin G (IgG), an antigen-binding fragment (Fab), a variable fragment (Fv), a single-chain fragment variable (scFv), an antibody with one V-gene domain, a bivalent diabody, and combinations thereof. In further embodiments, the candidate antigen-binding molecule is displayed on a bacteriophage (phage). In additional embodiments, the candidate antigen-binding molecule is derived from one or more hybridoma supernatants.

In embodiments, the invention provides multiplex methods of screening a candidate antigen-binding molecule for affinity to an antigen, comprising: (a) contacting the candidate antigen-binding molecule with a substrate, the substrate comprising (i) a plurality of antigens immobilized on the substrate, and (ii) a normalization binding molecule immobilized on the substrate; (b) detecting a binding of the candidate antigen-binding molecule with at least one of the plurality of antigens on the substrate; (c) detecting a binding of the candidate antigen-binding molecule from (b) to the immobilized normalization binding molecule to determine a concentration of the candidate antigen-binding molecule; and (d) determining the affinity of the candidate antigen-binding molecule from the binding of the candidate antigen molecule determined in (b) and the binding of the antigen-binding molecule to the normalization binding molecule determined in (c).

In certain aspects of the invention, the normalization binding molecule is an antibody or antigen binding fragment thereof that binds an epitope on the candidate antigen-binding molecule. In aspects wherein the candidate antigen-binding molecule is displayed on a phage, the normalization binding molecule can specifically bind to a phage protein.

BRIEF DESCRIPTION OF THE DRAWINGS

The following drawings form part of the present specification and are included to further demonstrate certain aspects of the present invention.

FIG. 1A-1C FIG. 1A is a schematic of 96-well four spot plate used in an embodiment of the invention.

DETAILED DESCRIPTION OF THE INVENTION

I. Definitions

As used herein, "a" or "an" may mean one or more. As used herein in the specification and claims, when used in conjunction with the word "comprising", the words "a" or "an" may mean one or more than one. As used herein, "another" or "a further" may mean at least a second or more.

As used herein, the term "about" is used to indicate that a value includes the inherent variation of error for the device, or the method being employed to determine the value.

As used herein, the term "plurality" means more than one type or kind of item (e.g., A and B), rather than just more than one of the same item (e.g., A and A). For example, the term "plurality of immobilized antigens," means that more than one antigen type is immobilized, not only that multiple copies of the same antigen are immobilized. However, in this example, the term "plurality of immobilized antigens," encompasses multiple copies of the same antigen as well as meaning more than one antigen type.

As used herein, the term "polypeptide" is intended to encompass a singular "polypeptide" as well as plural "polypeptides," and refers to a molecule composed of monomers (amino acids) linearly linked by amide bonds (i.e., peptide bonds). The term "polypeptide" refers to any chain or chains of amino acids and does not refer to a specific length of the product. Thus, peptides, oligopeptides, "protein," "amino acid chain," or any other term used to refer to a chain or chains of amino acids, are included within the definition of "polypeptide," and the term "polypeptide" may be used instead of or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology but is not necessarily translated from a designated nucleic acid sequence. It may be generated in any manner, including by chemical synthesis.

A "binding molecule," "antigen-binding molecule," or "normalization binding molecule" of the present invention refers to a molecule that specifically binds an antigenic determinant, for example, an antibody, an antibody fragment, or an antibody mimic. In embodiments, an antigen-binding molecule includes, but is not limited to, an affimer, an aptamer, an alphabody, an anticalin, an avimer, a DARPin, a fynomer, a Kunitz domain peptide, or a monobody. In another embodiment, a binding molecule of the invention is an antibody or an antigen binding fragment thereof that includes point mutations to increase affinity. In another embodiment, a binding molecule of the invention comprises at least one heavy or light chain complementarity determining region (CDR) of an antibody molecule. In another embodiment, a binding molecule of the invention comprises at least two CDRs from one or more antibody molecules. In another embodiment, a binding molecule of the invention comprises at least three CDRs from one or more antibody molecules. In another embodiment, a binding molecule of the invention comprises at least four CDRs from one or more antibody molecules. In another embodiment, a binding molecule of the invention comprises at least five CDRs from one or more antibody molecules. In another embodiment, a binding molecule of the invention comprises at least six CDRs from one or more antibody molecules.

Unless specifically referring to a full-length antibody, the term "antigen-binding molecule" and "normalization binding molecule" encompasses antigen-binding fragments, variants, analogs, or derivatives of an antibody, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press). Antibodies, immunoglobulins, and fragments thereof may be mammalian, vertebrate, human, murine, chicken, goat, rat, or may be derived from such antibodies, immunoglobulins, and fragments thereof.

The term "immunoglobulin" comprises various broad classes of polypeptides that can be distinguished biochemically. Those skilled in the art will appreciate that heavy chains are classified as gamma, mu, alpha, delta, or epsilon, with some subclasses among them (e.g., gamma1-gamma4). It is the nature of this chain that determines the "class" of the antibody as IgG, IgM, IgA IgD, IgE, or IgY, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention. The following discussion will generally be directed to the IgG class of immunoglobulin molecules. Regarding IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Mammalian light chains are classified as either kappa (Vκ) or lambda (Vλ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (mammalian Vκ or Vλ—collectively "VL") and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three-dimensional antigen binding site. This quaternary antibody structure forms the antigen binding site present at the end of each arm of the Y. More specifically, the antigen binding site is defined by three CDRs on each of the VH and VL chains. As used herein, the terms HCDR1, HCDR2, HCDR3 refer to VH CDR1, VH CDR2, VH CDR3, respectively. Likewise, as used herein, the terms LCDR1, LCDR2, LCDR3, refer to VL CDR1, VL CDR2, and VL CDR3, respectively. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three-dimensional configuration in an aqueous environment. The remainder of the amino acids in the antigen binding domains, referred to as "framework" regions, show less inter-molecular variability. The framework regions largely adopt a sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This region has been described by Kabat et al. (1983) U.S. Dept. of Health and Human Services, "Sequences of Proteins of Immunological Interest," by Chothia and Lesk, J. Mol. Biol. 196:901-917 (1987), and updated recently by Kunik et al., Nucl. Acids Res. 40:W521-W524 (2012), which are incorporated herein by reference, where the definitions include overlapping or subsets of amino acid residues when compared against each other. Nevertheless, application of any definition to refer to a CDR of an antibody or variants thereof is intended to be within the scope of the term as defined and used herein. The exact residue numbers that encompass a particular CDR will vary depending on the sequence and size of the CDR. Those skilled in the art can routinely determine which residues comprise a particular CDR given the variable region amino acid sequence of the antibody.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest."

Kunik et al., Nucl. Acids Res. 40:W521-W524 (2012) disclosed an online tool, Paratome, for systematic identification of antigen-binding regions in antibodies based on sequence or structure. Usually the Paratome-based analysis matches with Kabat numbering, but may also include residues adjacent to conventional CDRs.

Antibodies or antigen-binding fragments, variants, or derivatives thereof of the invention include, but are not limited to, polyclonal, monoclonal, multispecific, human, humanized, primatized, chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies. scFv molecules are known in the art and are described, e.g., in U.S. Pat. No. 5,892,019. Immunoglobulin or antibody molecules of the invention can be of any type, e.g., IgG, IgE, IgD, IgA, and IgY, class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

As used herein, the term "light chain portion" includes amino acid sequences derived from an immunoglobulin light chain, e.g., a kappa or lambda light chain. Preferably, the light chain portion comprises at least one of a VL or CL domain.

A "normalization binding molecule," defined above, may be described or specified in terms of the epitope(s) or portion(s) of a molecule that they recognize or specifically bind. The portion of a target polypeptide that specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for a normalization binding molecule is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by the normalization binding molecule of the present invention may contain a sequence of at least 4, at least 5, at least 6, at least 7, more preferably at least 8, at least 9, at least 10, at least 15, at least 20, at least 25, or between about 15 to about 30 contiguous or non-contiguous amino acids.

By "antigen" it is meant a substance that is capable of specifically or preferentially binding an antibody or antigen-binding fragment thereof.

By "specifically binds," it is meant that an antibody binds to an epitope via its antigen binding domain, and that the binding entails complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to preferentially bind a first epitope if it binds the first epitope with an equilibrium dissociation constant ($K_D$) that is less than the antibody's $K_D$ for a second epitope. In another non-limiting example, an antibody may be considered to preferentially bind a first antigen if it binds the first epitope with an affinity that is at least one order of magnitude less than the antibody's $K_D$ for a second epitope. In another non-limiting example, an antibody may be considered to preferentially bind a first epitope if it binds the first epitope with an affinity that is at least two orders of magnitude less than the antibody's $K_D$ for a second epitope.

In another non-limiting example, a candidate antigen-binding molecule or normalization binding molecule may be considered to preferentially bind a first epitope if it binds the first epitope with an off rate (k(off)) that is less than the antibody's k(off) for a second epitope. In another non-limiting example, an antibody may be considered to preferentially bind a first epitope if it binds the first epitope with an affinity that is at least one order of magnitude less than the antibody's k(off) for a second epitope. In another non-limiting example, an antibody may be considered to preferentially bind a first epitope if it binds the first epitope with an affinity that is at least two orders of magnitude less than the antibody's k(off) for a second epitope. An antibody or antigen-binding fragment, variant, or derivative disclosed herein may be said to bind a target antigen with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. In embodiments, an antigen-binding molecule or normalization binding molecule of the invention may be said to bind a target polypeptide disclosed herein with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$.

The candidate antigen-binding molecules and normalization binding molecules of the invention may be "multispecific," bispecific, trispecific, or of greater multispecificity, meaning that it recognizes and binds to two or more different epitopes present on one or more different antigens (e.g., proteins) at the same time. Thus, whether an antigen-binding molecule is "monospecific" or "multispecific," e.g., "bispecific," refers to the number of different epitopes with which a binding polypeptide reacts. Multispecific antibodies may be specific for different epitopes of a target or may be specific for a target polypeptide as well as for a heterologous epitope, such as a heterologous polypeptide.

As previously indicated, the subunit structures and three-dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al.). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked," "fused," or "fusion" are used interchangeably. These terms refer to the joining together of two or more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, an in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

II. Overview

The signal readout from a screening assay of candidate antigen-binding molecules for affinity to an antigen can depend both on actual candidate antigen-binding molecule binding affinity to an antigen, and on the concentration of the individual candidate antigen-binding molecule. The varying concentrations of individual candidate antigen-binding molecules thus provides a limitation on the screening assay.

For example, phage display is a popular method for in-vitro selection of candidate antigen-binding molecules that bind to specific antigens. In the most common phage display process, a mixture of phage particles each carrying a unique antibody fragment (for example, Fab or scFv) are selected by binding to immobilized antigen. Any unbound phage is washed away and bound phages re-infect E. coli, for example, and replicate. A typical selection process involves several rounds of selection and at the end of the experiment, individual phage clones are selected for expansion and characterization.

In a typical screening of selected phage clones, individual clones are inoculated into multi-well plates and grown overnight. Phage particles prepared from individual wells are testing by a binding assay such as ELISA. A limitation of the common screening format is that the identity of the candidate antigen-binding molecule influences the growth rate of individual clones, therefore the signal readouts from the screening assay not only depend on the affinity of the antigen antibody interaction but also depend on the growth properties of the individual phage clones.

Monoclonal antibody production involves screening of tissue culture supernatants from hybridomas, which can also vary in concentration of candidate antigen-binding molecule. In a typical monoclonal antibody production process, hybridoma cells grow in fusion wells and samples of tissue culture media (i.e., hybridoma supernatant) are removed from wells that have growing hybridomas. The hybridoma supernatants are then tested for the presence of the desired antibody. However, in some instances, even if the same amount of tissue culture media is removed from the well, the concentration of antibody can vary from sample to sample, which influences the signal readout from the screening assay. In addition, errors may be introduced with transferring the hybridoma supernatant to the screening assay platform.

III. Normalization Binding Molecule

The present invention addresses limitations in screening results based on varying concentrations of the candidate antigen-binding molecules. The present invention thus provides screening methods that use a normalization binding molecule that binds the candidate antigen-binding molecule, or in the case of phage display, binds a phage protein and/or a normalization binding molecule. Candidate antigen-binding molecule (or phage binding, in embodiments) binding to the normalization binding molecule is detected and used to determine the concentration of candidate antigen-binding molecule, increasing the accuracy of the binding affinity determination.

In embodiments, the invention thus provides methods of screening a candidate antigen-binding molecule for affinity to an antigen, comprising contacting a candidate antigen-binding molecule with a substrate, the substrate comprising (i) an antigen immobilized on the substrate, and (ii) a normalization binding molecule immobilized on the substrate; (b) detecting a binding of the candidate antigen-binding molecule with an antigen on the substrate; detecting a binding of the candidate antigen-binding molecule from (b) to the immobilized normalization binding molecule to determine a concentration of the candidate antigen-binding molecule; and (c) determining the affinity of the candidate antigen-binding molecule from the binding of the candidate antigen molecule determined in (b) and the binding of the antigen-binding molecule to the normalization binding molecule determined in (c).

In embodiments, the invention provides methods of screening a candidate antigen-binding molecule for affinity to an antigen, comprising contacting (1) a control compound at a plurality of concentrations, and (2) a candidate antigen-binding molecule with a substrate, the substrate comprising (i) an antigen immobilized on the substrate, and (ii) a normalization binding molecule immobilized on the substrate; detecting a binding of the candidate antigen-binding molecule with an antigen on the substrate; detecting a binding of the candidate antigen-binding molecule from (b) to the immobilized normalization binding molecule; detecting a binding of the control compound at the plurality of concentrations to the immobilized normalization binding molecule, wherein the detecting produces a plurality of detection signals; generating a standard calibration curve utilizing the plurality of detection signals; determining a first and a second concentration for each candidate antigen-binding molecule, wherein the first concentration is an apparent concentration determined from binding of the antigen-binding molecule to the immobilized antigen, and the second concentration is an actual concentration determined from the binding to the immobilized normalization binding molecule, wherein the actual concentration of each candidate antigen-binding molecule binding is determined using the calibration curve calculating a ratio of the first and second concentrations for each candidate molecule, wherein the ratio reflects the relative affinity of the antigen-binding molecule.

In embodiments, the control compound is bacteriophage, e.g., M13 bacteriophage, and the candidate antigen-binding molecules are displayed on bacteriophages. In embodiments, the control compound is an antibody, e.g., a high affinity antibody, and the candidate antigen-binding molecules are mutated antibodies, and optionally a parental wild type antibody.

In embodiments, the normalization binding molecule is an antibody or antigen-binding molecule that specifically or preferentially binds an epitope of the candidate antigen-binding molecule. The normalization binding molecule can also bind multiple epitopes on the candidate antigen-binding molecule. Thus, the term "specifically or preferentially binds an epitope" means specifically or preferentially binds at least one epitope. In embodiments, the normalization binding molecule specifically binds an epitope on the candidate antigen-binding molecule.

In embodiments, the epitope is present on about 100% of candidate antigen-binding molecules involved in the screening. In embodiments, the epitope is present on about 99%, about 98%, about 97%, about 96%, about 95%, about 94%, about 93%, about 92%, about 91%, about 90%, about 89%, about 88%, about 87%, about 86%, or about 85% of candidate antigen-binding molecules. In embodiments, the epitope is present on about 99-100%, about 98-99%, about 95%-99%, about 96-99%, about 95-99% or about 95-98% of candidate antigen-binding molecules.

In aspects of the invention, the epitope on the candidate antigen-binding molecule is a conserved region of an antibody, i.e., substantially the same throughout antibodies of the same type. For example, in aspects of the invention, the epitope on the candidate antigen-binding molecule is on a constant domain or fragment thereof of an antibody light chain or on a constant domain or fragment thereof of an antibody heavy chain. In embodiments, the epitope on the candidate antigen-binding molecule is on the CH1 domain. The epitope on the candidate antigen-binding molecule can thus, for example, be on a constant region or fragment thereof of a kappa light chain or a lambda light chain. In embodiments, the epitope of the candidate antigen-binding molecule is on the framework region, or a portion thereof, of an antibody light chain or an antibody heavy chain.

In embodiments, the normalization binding molecule binds to an epitope of the candidate antigen-binding molecule with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $8.4\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In embodiments, the $K_D$ is about $5\times10^{-9}$ M to about $6\times10^{-9}$ M. In further embodiments, the $K_D$ is about $1\times10^{-9}$ M to about $2\times10^{-9}$ M.

In embodiments, the invention provides methods of screening a candidate antigen-binding molecule for affinity to an antigen, wherein the antigen binding molecule is displayed on a bacteriophage ("phage"), discussed in more detail below. In the methods of the invention where the candidate antigen-binding molecule is displayed on a phage, the normalization binding molecule can be, for instance, an antibody or antigen binding fragment thereof that specifically or preferentially binds a phage. In embodiments, the normalization binding molecule binds a phage coat protein. Exemplary phage coat proteins include pIII, pVIII, pVII or pIX. In embodiments, the phage coat protein is a fusion protein. In embodiments wherein the antigen binding molecule is displayed on a bacteriophage ("phage"), the normalization binding molecule specifically or preferentially binds an epitope of the candidate antigen-binding molecule.

As is known in the art, addition of tags to antigen-binding molecules, e.g., antibodies, displayed on bacteriophages, or bacteriophage particles, or both, facilitates a variety of applications. For example, affinity tags aid in bacteriophage purification using affinity chromatography. Thus, in embodiments, the normalization binding molecule specifically binds an affinity tag on a phage that displays the candidate antigen-binding molecule or an affinity tag on the antigen-binding molecule, e.g., an antibody, displayed on the phage in the screening methods of the invention. Affinity tags on bacteriophages or antigen-binding molecules, e.g., antibodies, displayed on the bacteriophages include capsid-attached tags, since such tags typically do not interfere with adsorption and loss of infectivity. In embodiments, the tag is His-tag (a polyhistidine-containing tag), a FLAG-tag, a Strep II tag (STAG), or combinations thereof.

In embodiments, the normalization binding molecule specifically or preferentially binds an epitope on the phage. In embodiments, the epitope is on the phage coat protein. The normalization binding molecule can also bind multiple epitopes on the phage or phage coat protein. Thus, the term "specifically or preferentially binds an epitope" means specifically or preferentially binds at least one epitope.

In embodiments, the epitope is present on about 100% of phages involved in the screening. In embodiments, the epitope is present on about 99%, about 98%, about 97%, about 96%, about 95%, about 94%, about 93%, about 92%, about 91%, about 90%, about 89%, about 88%, about 87%, about 86%, or about 85% of phages. In embodiments, the epitope is present on about 99-100%, about 98-99%, about 95%-99%, about 96-99%, about 95-99% or about 95-98% of phages.

In aspects of the invention, the epitope on the phage is a conserved region of the phage, i.e., substantially the same throughout phages of the same type.

In embodiments, the normalization binding molecule specifically binds to an epitope of the display phage with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $8.4\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In embodiments, the $K_D$ is about $5\times10^{-9}$ M to about $6\times10^{-9}$ M. In further embodiments, the $K_D$ is about $1\times10^{-9}$ M to about $2\times10^{-9}$ M.

IV. Exemplary Assay Methods

In embodiments, the methods of the invention involve determining the affinity of a candidate-antigen binding molecule to an antigen by measuring the binding of a candidate antigen-binding molecule with an antigen and normalizing for the concentration of the candidate antigen-binding molecule. Such methods of the invention may be applied to singleplex or multiplex formats, i.e., where multiple assay measurements are performed on a single sample. Multiplex measurements that can be used with the invention include, but are not limited to, multiplex measurements that i) use multiple sensors; ii) use discrete assay domains on a surface (e.g., an array) that are distinguishable based on location on the surface; iii) use reagents coated on particles that are distinguishable based on a particle property such as size, shape, color, etc.; iv) produce assay signals that are distinguishable based on optical properties (e.g., absorbance or emission spectrum) or v) are based on temporal properties of assay signal (e.g., time, frequency or phase of a signal).

In embodiments, the screening methods of the invention are done in singleplex or multiplex. In certain singleplex embodiments, (a) candidate antigen-binding molecules are contacted with a first substrate containing immobilized antigen of a single type, followed by detecting binding of the candidate antigen-binding molecule to the antigen on the first substrate, and (b) candidate antigen-binding molecules are contacted with a second substrate containing immobilized normalization binding molecules, followed by detecting binding of the candidate antigen-binding molecule to the normalization binding molecule on the second substrate. In other singleplex embodiments, a single substrate containing immobilized antigen and immobilized normalization binding molecule is contacted with candidate antigen-binding molecule, followed by detection of binding of candidate antigen-binding molecule to the antigen and binding of the candidate antigen-binding molecule with the normalization binding molecule. In singleplex embodiments using multi-well plates, both the antigen and the normalization binding molecule can be immobilized to the substrate within a single well, thus eliminating potential pipetting error and increasing the throughput of the assay.

In certain multiplex embodiments, a substrate containing a plurality of immobilized antigens and immobilized normalization binding molecules is contacted with candidate antigen-binding molecules, and binding of candidate antigen-binding molecule to the plurality of antigens is detected, along with binding of candidate antigen-binding molecules to the normalization binding molecule. In a multiplex embodiment of the methods of the invention, one set of assays are run to determine candidate antigen-binding molecule binding affinity to a plurality of antigens, and another set of assays are run for normalization purposes. In a multiplex embodiment using multi-well plates, both the antigen and the normalization binding molecule can be immobilized to the substrate within a single well, thus eliminating potential pipetting error and increasing the throughput of the assay.

In embodiments, the multiplex methods of the invention are carried out using the methods for conducting multiplexed assays disclosed in US Patent Appl. Pub. No. 2016/0069872, published Mar. 10, 2016, which is herein incorporated by reference in its entirely. Thus, in embodiments, the invention provides methods that use a linking agent complex that enables configuration of an assay from a standard set of assay materials.

Techniques to determine the concentration of the candidate-antigen molecule from measurements of binding to a normalization molecule are known to those skilled in the art. For example, a control molecule having known concentrations can be assayed using the disclosed techniques. The detection signals from known dilutions of the control molecule can be used to back-calculate the concentration of the candidate antigen-binding molecule. The antigen binding measurements are then adjusted, i.e., normalized, for concentration using techniques well known in the art. Thus, high affinity candidate antigen-binding molecules having low concentration that may have been discarded would be ranked appropriately.

V. Candidate Antigen-Binding Molecule

As discussed above, an antigen-binding molecule in its broadest sense refers to a molecule that specifically binds an antigenic determinant. Therefore, in embodiments, the invention provides methods of determining whether one or more antigen-binding molecules specifically bind to an antigen. In embodiments, the antigen-binding molecule is an antibody fragment.

Examples of antibody fragments suitable for the methods of the invention include, without limitation: (i) the Fab fragment, consisting of VL, VH, CL, and CH1 domains; (ii) the "Fd" fragment consisting of the $V_H$ and $C_{H1}$ domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the VH and VL domains. Minibodies comprising a scFv joined to a CH3 domain may also be made (Hu et al., 1996). In embodiments, the candidate antigen-binding molecule is an scFv.

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

In embodiments, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). A hybridoma or other cell producing an antibody may also be subject to genetic mutation or other changes, which may or may not alter the binding specificity of antibodies produced by the hybridoma.

An antibody or preferably an immunological portion of an antibody, can be chemically conjugated to, or expressed as, a fusion protein with other proteins.

In embodiments, the candidate antigen-binding molecule specifically binds to an antigen of the candidate antigen-binding molecule with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $8.4 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In embodiments, the $K_D$ is about $5 \times 10^{-9}$ M to about $6 \times 10^{-9}$ M. In further embodiments, the $K_D$ is about $1 \times 10^{-9}$ M to about $2 \times 10^{-9}$ M.

The normalization methods of the invention are robust as shown in the Examples, and have been used to successfully screen and rank antigen-binding molecules against, for example, synthetic peptides (such as GLP-1, PYY, Ghrelin, C-peptide and Glucagon), as well as full length proteins (such as TNFa, IL-17A, IL-21, IL-23p19, G-CSF, IL-17F, MDC, IFN-g, IL-13, Eotaxin, PYY and MIP1-a).

A. Candidate Antigen Binding Molecule Displayed on Bacteriophage

Phage display is an effective way for producing large amounts of peptides, proteins and antibodies. This technology is based on the fact that phage phenotype and genotype are physically linked. The gene encoding the displayed molecule is packed within the same virion as a single-strained DNA (ssDNA) and the displayed peptides or proteins are expressed in fusion with phage coat protein. This genotype-phenotype linkage ensures that identical phage particles will be obtained from the same, for example, *Escherichia coli* clone. The phage display technique allows the creation of libraries which contain up to $10^{10}$ different variants and is used in affinity screening of cloned antigen-binding molecules, e.g., antibody repertoires.

Because of the phage display technology's ability to create antibody libraries that contain a great number of phage particles, from which each phage encodes and displays different molecules, a proper bio-panning procedure is needed for enriching the desired molecule level. The bio-panning method is based on repeated cycles of incubation, washing, amplification and reselection of bound phage. Several rounds of selection cycling are necessary to achieve the desired binding activity of monoclonal phage antibodies. For determining this activity several tests can be used in conjunction with the methods of the invention, for example enzyme-linked immunosorbent assay (ELISA), fluorometric microvolume assay technology (FMAT) or chromophore-assisted laser inactivation (CALI).

In embodiments, the invention provides methods of screening a candidate antigen-binding molecule for affinity to an antigen, wherein the antigen binding molecule is displayed on a bacteriophage ("phage") comprising contacting the phage with a substrate, the substrate comprising (i) an antigen immobilized on the substrate, and (ii) a normalization binding molecule immobilized on the substrate; (b) detecting a binding of a candidate antigen-binding molecule with an antigen on the substrate; and detecting a binding of the candidate antigen-binding molecule from (b) to the immobilized normalization binding molecule to determine a concentration of the candidate antigen-binding molecule; and (c) determining the affinity of the candidate antigen-binding molecule from the binding of the candidate antigen molecule determined in (b) and the binding of the antigen-binding molecule to the normalization binding molecule determined in (c).

Exemplary phages for displaying the candidate antigen-binding molecule are phages that infects the following bacteria: *Escherichia coli, Bacillus pumilus, Bacillus subtilis, Cellulosimicrobium cellulans, Oerskovia turbata, Pseudomonas aeruginosa, Pseudomonas syringae, Salmonella enterica* or *Thermus thermophilus*. In embodiments, the display phage is a phage that infects *Escherichia coli (E. coli)*. In embodiments, the phage is an *E. coli* filamentous bacteriophage. In embodiments, the *E. coli*-infecting phage is λ, M13, P1, T4, f1, fd or Mu. In embodiments, the phage displaying the candidate-antigen binding molecules of the invention is M13 or T4.

Many different antibody fragments are used in the phage display technology, including Fab (antigen-binding fragment), Fv (fragment variable), scFv (single chain fragment variable) and its modifications, antibodies with one V-gene domain, bivalent or bispecific diabodies and other oligomers. In Fab, VH-CH and VL-CL segments are linked by disulfide bonds and radiolabeled Fabs have found application in tumor imaging. An Fv molecule consists of the VL and VH regions only as well as its modification—the scFv, presently the most commonly used antibody fragment. Generally, the (Gly4Ser) linker is used to stabilize VL-VH connection and to ensure the proper antigen-binding site formation in scFv. These fragments have been expressed on phage surface without loss of antibody affinity. Furthermore, high binding affinity has been achieved by fusion of several different scFv segments. An example could be the CRAbs construct that consists of two scFv fragments specific to the same antigen but to adjacent epitopes. These fragments are connected by short linker (up to 10 amino acids), thereby dimerization of molecules and diabodies forming is possible.

In embodiments, when candidate antigen-binding molecules are displayed on a phage, antigen is bound on a substrate that comprises multiple copies of the same antigen, or a plurality of immobilized antigens, i.e., more than one antigen type is immobilized on the substrate, not just multiple copies of the same antigen. In embodiments, the substrate is a multi-well plate or a microparticle. In embodiments when the candidate antigen-binding molecule is displayed on a phage, the substrate also comprises a normalization antibody that binds an epitope on the candidate antigen-binding molecule, discussed in more detail herein. In such embodiments, the substrate is a multi-well plate or a microparticle.

The normalization methods of the invention are robust as shown in the Examples, and have been used to successfully screen and rank phage display clones against, for example, synthetic peptides (such as GLP-1, PYY, Ghrelin, C-peptide and Glucagon), as well as full length proteins (such as TNFa, IL-17A, IL-21, IL-23p19, G-CSF, IL-17F, MDC, IFN-g, IL-13, Eotaxin, PYY and MIP1-a).

B. Candidate Antigen Binding Molecule Derived from Hybridoma Supernatants

Hybridoma technology is a well-known method for producing large numbers of identical antibodies, i.e., monoclonal antibodies. The process typically begins by injecting a mouse or other mammal with an antigen that provokes the production of B cells, which produce antibodies that bind to the antigen. The B-cells are isolated and fused with a myeloma to produce the hybridoma. The hybridomas can be grown in culture, which produces one antibody per culture. The antibodies are secreted into the culture medium, also called the supernatant.

In embodiments, the methods of the invention screen a candidate antigen-binding molecule that is derived from the hybridoma supernatant for affinity to an antigen.

The present invention thus provides methods of screening candidate antigen-binding molecules derived from hybridoma supernatants for their binding to antigens. In embodiments, the method comprises contacting candidate antigen-binding molecules derived from a hybridoma supernatant with a substrate, the substrate comprising (i) an antigen immobilized on the substrate, and (ii) a normalization binding molecule immobilized on the substrate; detecting a binding of a candidate antigen-binding molecule with the antigen on the substrate; detecting a binding of the candidate antigen-binding molecule from (b) to the immobilized normalization binding molecule to determine a concentration of the candidate antigen-binding molecule; and determining the affinity of the candidate antigen-binding molecule from the binding of the candidate antigen molecule determined in (b) and the binding of the antigen-binding molecule to the normalization binding molecule determined in (c).

In embodiments where the antigen-binding molecule is derived from a hybridoma supernatant, antigen is bound on a substrate that comprises multiple copies of the same antigen, or a plurality of immobilized antigens, i.e., more than one antigen type is immobilized on the substrate, not only multiple copies of the same antigen. In embodiments, the substrate is a multi-well plate or a microparticle. In embodiments when the candidate antigen-binding molecule is derived from an antibody supernatant, the substrate also comprises a normalization antibody that binds an epitope on the candidate antigen-binding molecule, discussed in more detail infra. In embodiments, the substrate is a multi-well plate or a microparticle.

VI. Substrate

As discussed elsewhere, in embodiments, the methods of the invention use a substrate, typically, a solid surface, that contains an immobilized antigen and an immobilized normalization binding molecule. Suitable substrates are known to those skilled in the art. For example, multi-well plates and microparticles are both suitable substrates for use in the claimed invention. In embodiments, multi-well plates containing 6, 12, 24, 48, 96, 384 or 1536 wells or more are suitable for use in the screening methods of the invention. Microparticles, e.g., beads, are likewise suitable for the screening methods of the invention.

Suitable substrates for use in the methods of the present invention include conventional solid phases from the art of binding assays. Solid phases may be made from a variety of different materials including polymers (e.g., polystyrene and polypropylene), ceramics, glass, composite materials (e.g., carbon-polymer composites such as carbon-based inks). Suitable solid phases include the surfaces of macroscopic objects such as an interior surface of an assay container (e.g., test tubes, cuvettes, flow cells, microfluidic channels, capillaries (e.g., ELLA glass nano-reactors from BioTechne), FACS cell sorter, cartridges, wells in a multi-well plate, etc.), slides, assay chips (such as those used in gene or protein chip measurements), pins or probes, beads, filtration media, lateral flow media (for example, filtration membranes used in lateral flow test strips), etc.

Suitable substrates also include particles (including but not limited to colloids or beads) commonly used in other types of particle-based assays e.g., magnetic, polypropylene, and latex particles, materials typically used in solid-phase synthesis e.g., polystyrene and polyacrylamide particles, and materials typically used in chromatographic applications e.g., silica, alumina, polyacrylamide, polystyrene. The materials may also be a fiber such as a carbon fibril. Microparticles may be inanimate or alternatively, may include animate biological entities such as cells, viruses, bacterium and the like. A particle used in the present method may be comprised of any material suitable for attachment to one or more binding reagents, and that may be collected via, e.g., centrifugation, gravity, filtration or magnetic collection. A wide variety of different types of particles that may be attached to binding reagents are sold commercially for use in binding assays. These include non-magnetic particles as well as particles comprising magnetizable materials which allow the particles to be collected with a magnetic field. In one embodiment, the particles are comprised of a conductive and/or semiconductive material, e.g., colloidal gold particles. The microparticles may have a wide variety of sizes and shapes. By way of example and not limitation, microparticles may be between 5 nanometers and 100 micrometers. Preferably microparticles have sizes between 20 nm and 10 micrometers. The particles may be spherical, oblong, rod-like, etc., or they may be irregular in shape.

The particles used in the present method may be coded to allow for the identification of specific particles or subpopulations of particles in a mixture of particles. The use of such coded particles has been used to enable multiplexing of assays employing particles as solid phase supports for binding assays. In one approach, particles are manufactured to include one or more fluorescent dyes and specific populations of particles are identified based on the intensity and/or relative intensity of fluorescence emissions at one or more wave lengths. This approach has been used in the Luminex xMAP systems (see, e.g., U.S. Pat. No. 6,939,720) and the Becton Dickinson Cytometric Bead Array systems. Alternatively, particles may be coded through differences in other physical properties such as size, shape, imbedded optical patterns and the like. One or more particles provided in a mixture or set of particles may be coded to be distinguishable from other particles in the mixture by particle optical properties, size, shape, imbedded optical patterns and the like.

The antigen and the normalization binding molecule are immobilized on the substrate using techniques known to one of skill in the art, for example, via linker molecules, such as biotin complexed with streptavidin, and/or targeting agents and targeting agent complements with or without bridging agents. For example, the substrate may be coated with streptavidin, and the antigen or normalization binding molecule of interest is biotinylated. The antigen therefore is immobilized on the substrate via the streptavidin-biotin complex. In additional embodiments, targeting agents bound to linking agents with or without bridging agents can be used to immobilize antigen and the normalization binding molecule, as disclosed in US Pat. Publ. No. 2016/0069872, the disclosure of which is incorporated herein by reference in its entirety. The binding molecules can be bound via targeting agents to different discrete binding domains on one or more solid phases, e.g., as in an array, such that discrete assay signals are generated on each binding domain and therefore, the different analytes bound to those domains can be measured independently. In one example of such an embodiment, the binding domains are prepared by immobilizing, on one or more surfaces, discrete domains of targeting agents that, through complex of targeting agent complement, a linking agent, supplemental linking agent, and with or without a bridging agent, built on the individual domains, are configured to bind analytes of interest, e.g., antigen and normalization binding molecule.

In embodiments, in the methods of the invention, the antigen is immobilized on the substrate surface via a targeting agent bound to the surface and a targeting agent complement indirectly bound to the antigen. The term "indirectly bound" in this context indicates that the targeting agent complement is linked to the antigen by at least one intervening molecule. For instance, in embodiments, the targeting agent complement is additionally bound to a linking agent, and the antigen is bound to a supplemental linking agent, wherein the linking agent and the supplemental linking agent are binding partners.

In further embodiments, in the methods of the invention, the normalization binding molecule is immobilized on the substrate surface via a targeting agent bound to the surface and a targeting agent complement indirectly bound to the normalization binding molecule. The term "indirectly bound" in this context indicates that the targeting agent complement is linked to the normalization binding molecule by at least one intervening molecule. For example, in embodiments, the targeting agent complement is additionally bound to a linking agent, and the normalization binding molecule is bound to a supplemental linking agent, wherein the linking agent and the supplemental linking agent are binding partners.

In additional embodiments, the intervening molecule discussed above additionally comprises a bridging agent, wherein the bridging agent has a first binding site for the linking agent, and a second binding site for the supplemental linking agent.

Exemplary targeting agents, targeting agent complements, linking agents, supplemental linking agents, and bridging agents are disclosed in US Pat. Publ. No. 2016/0069872.

Optionally, the surface(s) may define, in part, one or more boundaries of a container (e.g., a flow cell, well, cuvette, etc.) which holds the sample or through which the sample is passed. In a preferred embodiment, individual binding domains are formed on electrodes for use in electrochemical or electrochemiluminescence assays. Multiplexed measurement of analytes on a surface comprising a plurality of binding domains using electrochemiluminescence has been used in the Meso Scale Diagnostics, LLC, MULTI-ARRAY® and SECTOR® Imager line of products (see, e.g., U.S. Pat. Nos. 7,842,246 and 6,977,722, the disclosures of which are incorporated herein by reference in their entireties).

VII. Assay Devices

The methods of the present invention may be used in a variety of assay devices and/or formats. The assay devices may include, e.g., assay modules, such as assay plates, cartridges, multi-well assay plates, reaction vessels, test tubes, cuvettes, flow cells, assay chips, lateral flow devices, etc., having assay reagents (which may include targeting agents or other binding reagents) added as the assay progresses or pre-loaded in the wells, chambers, or assay regions of the assay module. These devices may employ a variety of assay formats for specific binding assays, e.g., immunoassay or immunochromatographic assays. Illustrative assay devices and formats are described herein below. In certain embodiments, the methods of the present invention may employ assay reagents that are stored in a dry state and the assay devices/kits may further comprise or be supplied with desiccant materials for maintaining the assay reagents in a dry state. The assay devices preloaded with the assay reagents can greatly improve the speed and reduce the complexity of assay measurements while maintaining excellent stability during storage. The dried assay reagents may be any assay reagent that can be dried and then reconstituted prior to use in an assay. These include, but are not limited to, binding reagents useful in binding assays, enzymes, enzyme substrates, indicator dyes and other reactive compounds that may be used to detect an analyte of interest. The assay reagents may also include substances that are not directly involved in the mechanism of detection but play an auxiliary role in an assay including, but not limited to, blocking agents, stabilizing agents, detergents, salts, pH buffers, preservatives, etc. Reagents may be present in free form or supported on solid phases including the surfaces of compartments (e.g., chambers, channels, flow cells, wells, etc.) in the assay modules or the surfaces of colloids, beads, or other particulate supports.

VIII. Measurement Methods

The methods of the invention can be used with a variety of methods known in the art for measuring the amount of an analyte bound to molecules immobilized on a substrate, e.g., the amount of candidate antigen-binding molecule bound to antigen and the amount of candidate antigen-binding molecule bound to the normalization binding molecule. Techniques that may be used include, but are not limited to, techniques known in the art such as cell culture-based assays, binding assays (including agglutination tests, immunoassays, nucleic acid hybridization assays, etc.), enzymatic assays, colorimetric assays, etc. Other suitable techniques will be clear to one of average skill in the art. Some measurement techniques allow for measurements to be made by visual inspection, others may require or benefit from the use of an instrument to conduct the measurement.

Methods for measuring the amount of an analyte include label free techniques, which include but are not limited to i) techniques that measure changes in mass or refractive index at a surface after binding of an analyte to a surface (e.g., surface acoustic wave techniques, surface plasmon resonance sensors, ellipsometric techniques, etc.), ii) mass spectrometric techniques (including techniques like MALDI, SELDI, etc. that can measure analytes on a surface), iii) chromatographic or electrophoretic techniques, iv) fluorescence techniques (which may be based on the inherent fluorescence of an analyte), etc.

Methods for measuring the amount of an analyte also include techniques that measure analytes through the detection of labels which may be attached directly or indirectly (e.g., using labeled binding partners of an analyte) to an analyte. Suitable labels include labels that can be directly visualized (e.g., particles that may be seen visually and labels that generate measurable signal such as light scattering, optical absorbance, fluorescence, chemiluminescence, electrochemiluminescence, radioactivity, magnetic fields, etc.). Labels that may be used also include enzymes or other chemically reactive species that have a chemical activity that leads to a measurable signal such as light scattering, absorbance, fluorescence, etc. The use of enzymes as labels has been well established in Enzyme-Linked ImmunoSorbent Assays, also called ELISAs, Enzyme ImmunoAssays or EIAs. In the ELISA format, an unknown amount of antigen is affixed to a surface and then a specific antibody is washed over the surface so that it can bind to the antigen. This antibody is linked to an enzyme, and in the final step a substance is added that the enzyme converts to a product that provides a change in a detectable signal. The formation of product may be detectable, e.g., due a difference, relative to the substrate, in a measurable property such as absorbance, fluorescence, chemiluminescence, light scattering, etc. Certain (but not all) measurement methods that may be used with solid phase binding methods according to the invention may benefit from or require a wash step to remove unbound components (e.g., labels) from the solid phase Accordingly, the methods of the invention may comprise such a wash step.

In embodiments, an analyte(s) of interest in the sample may be measured using electrochemiluminescence-based assay formats, e.g. electrochemiluminescence (ECL) based immunoassays. The high sensitivity, broad dynamic range and selectivity of ECL are important factors for research and for medical diagnostics. Commercially available ECL instruments have become widely used for reasons including their sensitivity, dynamic range, precision, and tolerance of complex sample matrices. Species that can be induced to emit ECL (ECL-active species) have been used as ECL labels, e.g., i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485), oxalate, and persulfate for ECL from RuBpy and hydrogen peroxide for ECL from luminol (see, e.g., U.S. Pat. No. 5,240,863). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels, ECL assays and instrumentation for conducting ECL assays see U.S. Pat. Nos. 5,093,268; 5,147, 806; 5,324,457; 5,591,581; 5,597,910; 5,641,623; 5,643, 713; 5,679,519; 5,705,402; 5,846,485; 5,866,434; 5,786, 141; 5,731,147; 6,066,448; 6,136,268; 5,776,672; 5,308, 754; 5,240,863; 6,207,369; 6,214,552 and 5,589,136 and Published PCT Nos. WO99/63347; WO00/03233; WO99/58962; WO99/32662; WO99/14599; WO98/12539; WO97/36931 and WO98/57154, all of which are incorporated herein by reference.

In embodiments, the detection methods of the invention use distinctly colored bead sets as substrate, which are created by two fluorescent dyes at distinct ratios. These beads can be further conjugated with a reagent specific to the bioassay. The technology enables multiplex immunoassays in which one antibody to a specific analyte is attached to a set of beads with the same color, and the second antibody to the analyte is attached to a fluorescent reporter dye label. The use of different colored beads enables the simultaneous multiplex detection of other analytes in the same sample. A dual detection flow cytometer is used to sort out the different assays by bead colors in one channel and determine the analyte concentration by measuring the reporter dye fluorescence in another channel.

During data acquisition, the contents of each microplate well are drawn into the array reader, depending on the type of reader—either the flow cytometry/laser excitation—based Bio-Plex 200 and Bio-Plex 3D systems or the light emitting diode (LED)/image-based analysis employed in the Bio-Plex® MAGPIX™ multiplex reader. For the flow cytometry-based systems, fluidics align the beads in single file through a flow cell where two lasers excite the beads individually. The red classification laser excites the dyes in each bead, identifying its spectral address. The green reporter laser excites the reporter molecule associated with the bead, which allows quantitation of the captured analyte. With the LED/image-based Bio-Plex MAGPIX reader, the beads are drawn into a chamber and magnetically immobilized. Classification and reporter excitation are accomplished with the use of LEDs rather than lasers. In all readers, high-speed digital signal processors and software record the fluorescent signals simultaneously for each bead, translating the signals into data for each bead-based assay.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods ID Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods ID Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (WIT. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al, (2001) Immunology (6th ed.; London: Mosby); Abbas et al, (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

IX. Examples

Example 1—Screening M13 Phage Display Clones

A library of mutant mouse kappa light chain antibodies in Fab format was selected against immobilized GLP-1 conjugated to bovine serum albumin target. After selection, clones from the selection output were randomly picked and grown up in a 96-well plate and culture media containing phage particles were tested using a Meso Scale Diagnostics (MSD) assay.

Figure 1A:
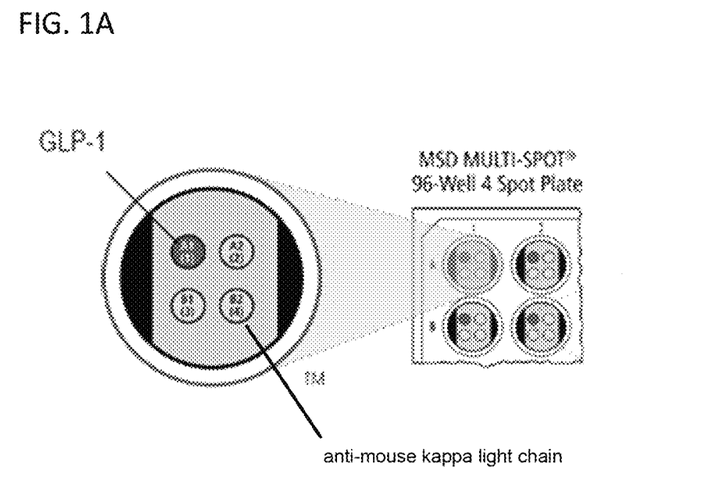
Figure 1B:
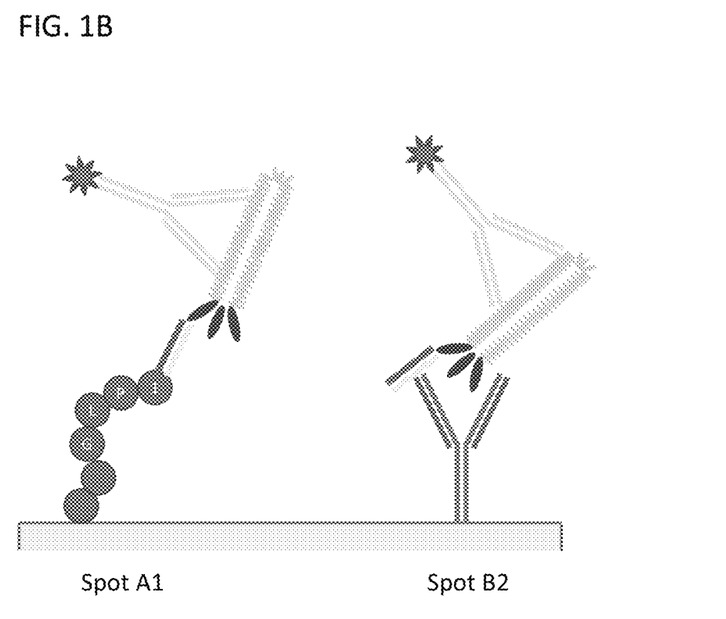
FIG. 1B is a schematic of an example sandwich format for phage display.

An MSD MULTI-SPOT plate bottom was spotted with 2 ug/ml GLP-1 conjugated bovine serum albumin on spot A1 and 100 ug/ml rat anti-mouse kappa light chain antibody (H139.52.1) on spot B2 (see FIG. 1A). (2) Overnight culture medium of phage was diluted 1:10 in 1% bovine serum albumin. Diluted phage was added to wells and incubated for 2 hours at room temperature. After washing, rabbit anti-M13 detection was added for 1 hour at room temperature. The plate was then washed and 1×MSD read buffer was added followed by plate reading.

In this example, 80 phage clones from the selection experiment were grown in 96 well plates. Positive phage controls were run in duplicate in 3-fold dilutions on the same MSD plate. Assay results are shown in Table 1.

TABLE 1

| | 1 | 2 | 3 | 4 | 5 | 6 | 7 | 8 | 9 | 10 | Positive control | |
|---|---|---|---|---|---|---|---|---|---|---|---|---|
| | | | | | | GLP1-BSA | | | | | | |
| A | 16241 | 10618 | 493 | 361 | 674 | 57545 | 6249 | 600 | 411 | 784 | 38340 | 42203 |
| B | 7441 | 51808 | 60026 | 8284 | 16061 | 19616 | 23302 | 9481 | 2150 | 6749 | 27322 | 14399 |
| C | 732 | 9042 | 2235 | 398 | 2738 | 566 | 12519 | 9730 | 21497 | 6519 | 6993 | 7436 |
| D | 2708 | 9093 | 1031 | 18756 | 1549 | 527 | 299 | 10185 | 15437 | 576 | 1832 | 2151 |
| E | 703 | 1007 | 5271 | 6704 | 525 | 12118 | 23431 | 346 | 9315 | 8165 | 699 | 573 |
| F | 15707 | 934 | 22282 | 6279 | 2233 | 149 | 8865 | 15989 | 42556 | 25252 | 254 | 272 |
| G | 832 | 9481 | 676 | 527 | 1641 | 548 | 9050 | 3755 | 288 | 329 | 157 | 148 |
| H | 718 | 12374 | 6067 | 3599 | 12740 | 7057 | 11939 | 10087 | 280 | 21156 | 84 | 102 |
| | | | | | | anti-kappa | | | | | | |
| A | 13366 | 9954 | 665 | 540 | 1017 | 43302 | 17505 | 615 | 523 | 871 | 62622 | 72535 |
| B | 14311 | 24110 | 29686 | 4643 | 12221 | 10341 | 13062 | 4581 | 9355 | 5603 | 17969 | 12444 |
| C | 6288 | 9088 | 5286 | 2449 | 16679 | 749 | 10537 | 14752 | 11576 | 18693 | 5978 | 6511 |
| D | 6829 | 12515 | 6554 | 7735 | 10881 | 3735 | 2171 | 5782 | 9532 | 3419 | 1756 | 1869 |
| E | 739 | 3225 | 4056 | 10209 | 689 | 9388 | 9481 | 571 | 4794 | 13601 | 592 | 661 |
| F | 11044 | 1037 | 9778 | 22015 | 1923 | 4837 | 11190 | 4845 | 14962 | 9708 | 270 | 241 |
| G | 1215 | 3628 | 695 | 848 | 1307 | 802 | 3636 | 4644 | 490 | 495 | 185 | 203 |
| H | 871 | 6079 | 2786 | 14185 | 9912 | 3689 | 4332 | 2182 | 8394 | 6063 | 133 | 131 |

Ranking of phage clones after adjustment for difference in phage concentration are shown in Table 2. Positive control on anti-kappa spot in Table 1 was used to generate a standard curve for phage concentration determination. The highest concentration of positive control was arbitrary assigned as one. Relative concentration of phage in each well was calculated by MSD Workbench software. GLP1 specific signals generated by the phage were then adjusted to the relative phage concentration and ranked in Table 2.

TABLE 2

| | GLP1 signal | Fab signal | calculated phage conc | GLP1/phage |
|---|---|---|---|---|
| 2H08 | 10087 | 2182 | 0.0233 | 432752 |
| 2H10 | 21156 | 6063 | 0.0612 | 345932 |

TABLE 2-continued

| | GLP1 signal | Fab signal | calculated phage conc | GLP1/phage |
|---|---|---|---|---|
| 2F08 | 15989 | 4845 | 0.0496 | 322060 |
| 2F09 | 42556 | 14962 | 0.1404 | 303185 |
| 2F10 | 25252 | 9708 | 0.0944 | 267429 |
| 2H07 | 11939 | 4332 | 0.0447 | 266991 |
| 2E07 | 23431 | 9481 | 0.0924 | 253600 |
| 2G02 | 9481 | 3628 | 0.0379 | 250440 |
| 2D04 | 18756 | 7735 | 0.0766 | 244845 |
| 2B02 | 51808 | 24110 | 0.2169 | 238810 |

Example 2—Calculating Affinity Normalizing for Phage Concentration

The top five ranked phage clones from Example 1 were selected for further characterization. New phage preparations were prepared and the assay was run in duplicate with 2-fold dilutions. Average assay results are shown in Table 3.

TABLE 3

| | WT | 2F08 | 2F09 | 2F10 | 2H08 | 2H10 |
|---|---|---|---|---|---|---|
| | | | GLP1-BSA | | | |
| ¼× | 5045 | 13542 | 39778 | 8724 | 4979 | 9160 |
| ⅛× | 2455 | 6607 | 18814 | 4652 | 2604 | 4189 |
| 1/16× | 1225 | 3241 | 9117 | 2312 | 1360 | 2320 |

TABLE 3-continued

| | WT | 2F08 | 2F09 | 2F10 | 2H08 | 2H10 |
|---|---|---|---|---|---|---|
| 1/32× | 645 | 1535 | 4239 | 1144 | 733 | 1237 |
| 1/64× | 323 | 813 | 2041 | 617 | 386 | 613 |
| | | | anti-kappa normalization | | | |
| ¼× | 1652 | 2292 | 6799 | 1608 | 975 | 2505 |
| ⅛× | 718 | 866 | 2721 | 1162 | 518 | 946 |
| 1/16× | 387 | 462 | 1422 | 460 | 286 | 592 |
| 1/32× | 207 | 250 | 729 | 324 | 173 | 328 |
| 1/64× | 114 | 132 | 342 | 147 | 83 | 194 |

Based on the calibration curve of the wild type phage (WT), the relative concentrations of individual phage clones were back calculated using MSD workbench software. Two concentrations for each phage are calculated: first, the apparent concentration calculated from the GLP-1 spot and second, the real concentration calculated from the anti-kappa spot. The ratios of the two calculated concentrations reflect the relative affinity of individual phage clones. Wild type phage should have a ratio of one and if the ratio of a mutant phage clone is >1, then the binding of this mutant phage to GLP-1 antigen is stronger compared to wild type phage. The results are shown in Table 4. Data outside the range of calibration curve was removed.

TABLE 4

| | GLP1-BSA/anti-kappa (back calculation) | | | | | |
|---|---|---|---|---|---|---|
| | WT | 2F08 | 2F09 | 2F10 | 2H08 | 2H10 |
| $1/4\times$ | 1.00 | 2.14 | | 1.81 | 1.60 | 1.28 |
| $1/8\times$ | 1.05 | 2.38 | 2.71 | 1.27 | 1.52 | 1.38 |
| $1/16\times$ | 0.96 | 2.11 | 2.12 | 1.52 | 1.45 | 1.19 |
| $1/32\times$ | 0.98 | 1.89 | 1.78 | 1.07 | 1.38 | 1.15 |
| $1/64\times$ | 1.02 | 2.21 | 1.80 | 1.42 | | 1.00 |

In this MULTI-SPOT MSD assay format, in addition to binding data to targeted antigen (GLP-1), additional data for phage concentration generated by anti-kappa antibody coated spot was used to normalize and compensate for the GLP-1 spot signal difference due to variation in concentration of phage in individual wells. Without normalization data, high affinity phage clones with low concentration would have been disregarded because of the low signal level observed in the GLP-1 coated spot. To overcome this problem without a normalization method, it is a common practice in the phage display field to set a low threshold for accepting more positive clones. All the positive clones will be expressed and purified as antibody, quantified and then compared.

The normalization method described in this Example was used to successfully screen and rank phage display clones against the following antigens: TNFa human, IL-17A human, IL-21 human, IL-23p19 human, G-CSF human, Glucagon human, IL-17F human, MDC human, IFN-g human, IL-13 human, Eotaxin human, PYY human, C-peptide human, Ghrelin human and MIP1-a human.

The current method introduced normalization and increased the accuracy of the screening; therefore it is possible to reduce the number of clones to be converted and purified as antibodies for further testing, which significantly saves time and effort for the screening process.

Although it is possible to run the assay in duplicate, i.e., one set of assays to address antigen antibody affinity and another set of assays to address concentration of phages in individual wells for normalization purpose, this would reduce throughput by half and introduce pipetting errors. Instead, the assay format in this example records all the data in the same well, which eliminated potential pipetting error and increased the throughput of the assay.

Example 3—Multiplexed Screening of Hybridoma Supernatants for Monoclonal Antibody Development Against TH17 Related Cytokines The antigens used in this study represented Th17-related cytokines that mediate a host's defense mechanisms against various infections and cancer and play a crucial role in crosstalk between the immune system and affected tissues.

To develop new monoclonal antibodies against these targets, we employed traditional hybridoma technology combined with screening on electrochemiluminescence-based MULTI-ARRAY® platform of Meso Scale Discovery. The use of MSD MULTI-SPOT® plates enabled parallel multiplexed screening of hybridoma culture supernatants against specific and unrelated antigens as well as performing more than one assay format with different ways of antigen immobilization in the same well of a 96 well microtiter plate, a process that is not possible with the conventional ELISA-based screening methods.

For most antigens, the subsets of hybridoma clones detected by each assay format were overlapping, but not identical. For some targets the way the antigen was immobilized on the surface was important for identification of antigen-specific hybridoma clones, and one of the assay formats was unable to detect the vast majority of positive hybridoma clones detected by another assay format. None of the assay formats employing different immobilization of the antigen on the surface was vastly superior to the others, and the simultaneous use of more than one assay format is required to detect the maximum number of antigen-specific hybridoma clones. For each target 10-100 new hybridoma clones were identified with antibodies recognizing at least two or more different epitopes on the target. New antibody pairs for MSD assays with sensitivities of 1 pg/mL or below for many targets were identified.

Multiplexed primary screening of hybridoma supernatants using multiple assay formats is superior to the traditional singleplexed screening approaches. The use of only one assay format in screening could result in missing valuable hybridoma clones.

Advantageously, the methods described herein for screening a candidate antigen-binding molecule for affinity to an antigen can also be applied to the screening in this example.

Example 4—Screening Genetically Modified GLP-1 Antibodies in IgG1 Format

Six mouse anti GLP-1 antibodies were tested against control GLP-1 antibody in IgG1 format.

Figure 1C:
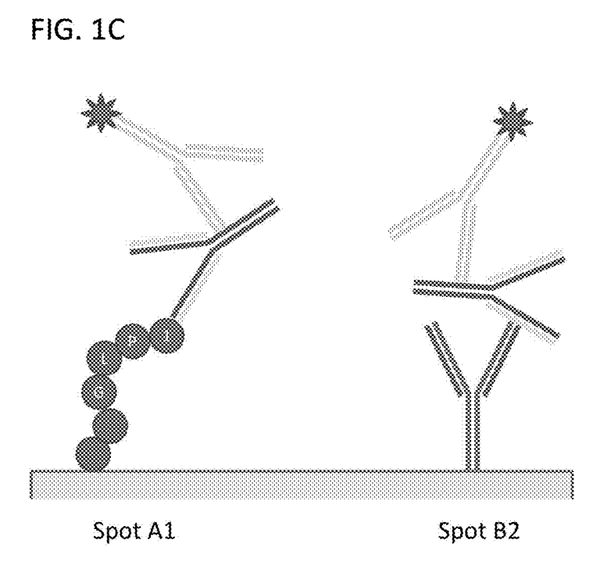
FIG. 1C is a schematic of an example assay of the invention utilizing an IgG format.

An MSD MULTI-SPOT plate bottom was spotted with 500 µg/ml streptavidin on spot A1 and 100 µg/ml goat anti-mouse antibody on another spot (FIG. 1C). 1 nM biotinylated GLP-1 was then captured on the streptavidin spot. After washing, serial diluted test mutant GLP-1 antibodies and control GLP-1 antibody were added to wells and incubated for 1 hour at room temperature. After washing, goat anti-IgG detection was added for 1 hour at room temperature. The plate was then washed and 2×MSD read buffer was added followed by plate reading.

Positive control and test antibodies were run in triplicate in 2-fold dilutions on the same MSD plate. Assay results are shown in Table 5. In this example, a high affinity GLP-1 antibody was used as positive control and five mutants and their parental wild type antibody were tested against each other.

TABLE 5

Plate layout

| | test IgGs | | | 2× dilution standard curve |
|---|---|---|---|---|
| A | Mutant 1 (250× diluted) | Mutant 2 (250× diluted) | Mutant 3 (250× diluted) | |
| B | Mutant 1 (500× diluted) | Mutant 2 (500× diluted) | Mutant 3 (500× diluted) | |
| C | Mutant 1 (1000× diluted) | Mutant 2 (1000× diluted) | Mutant 3 (1000× diluted) | |
| D | Mutant 1 (2000× diluted) | Mutant 2 (2000× diluted) | Mutant 3 (2000× diluted) | |
| E | Mutant 4 (250× diluted) | Mutant 5 (250× diluted) | wild type (250× diluted) | |
| F | Mutant 4 (500× diluted) | Mutant 5 (500× diluted) | wild type (500× diluted) | |
| G | Mutant 4 (1000× diluted) | Mutant 5 (1000× diluted) | wild type (1000× diluted) | |
| H | Mutant 4 (2000× diluted) | Mutant 5 (2000× diluted) | wild type (2000× diluted) | |

| | test IgGs | | | | | | | | | control GLP-1 IgG | | |
|---|---|---|---|---|---|---|---|---|---|---|---|---|
| | GLP-1 | | | | | | | | | | | |
| A | 32790 | 33937 | 32845 | 107647 | 105106 | 110361 | 69033 | 66796 | 61247 | 225528 | 286007 | 265436 |
| B | 19422 | 18262 | 16931 | 54728 | 58682 | 60036 | 40615 | 36236 | 35353 | 147511 | 154736 | 164155 |
| C | 10707 | 9745 | 9113 | 28046 | 27747 | 33366 | 20232 | 18978 | 17810 | 82963 | 80852 | 88527 |
| D | 5465 | 5222 | 4838 | 14774 | 15181 | 15405 | 10349 | 10012 | 9676 | 42413 | 47174 | 45256 |
| E | 84192 | 84261 | 83517 | 94809 | 93646 | 103285 | 63265 | 57092 | 49153 | 21056 | 24722 | 24311 |
| F | 51677 | 46493 | 44269 | 50347 | 52275 | 55898 | 35063 | 32170 | 32042 | 13633 | 13986 | 13210 |
| G | 24046 | 28256 | 25164 | 30319 | 29414 | 29747 | 16677 | 18543 | 16545 | 6376 | 7707 | 6873 |
| H | 12287 | 13788 | 13748 | 15865 | 14564 | 16215 | 9869 | 8384 | 8766 | 3516 | 3918 | 4008 |
| | goat anti-IgG | | | | | | | | | | | |
| A | 120042 | 113948 | 124585 | 128842 | 121869 | 125585 | 88978 | 89412 | 88326 | 342431 | 358114 | 315801 |
| B | 61300 | 62895 | 65460 | 68049 | 63712 | 67156 | 47512 | 47732 | 46138 | 192457 | 185406 | 195803 |
| C | 31696 | 32606 | 33316 | 35320 | 34182 | 34343 | 24966 | 25112 | 23448 | 97305 | 107065 | 102999 |
| D | 16472 | 16359 | 16773 | 17207 | 17826 | 17733 | 12726 | 12197 | 12354 | 52813 | 51962 | 51640 |
| E | 106669 | 106426 | 103556 | 120139 | 127959 | 126855 | 234630 | 248680 | 243721 | 27473 | 27854 | 26191 |
| F | 57006 | 56605 | 59183 | 65384 | 66865 | 63811 | 135331 | 129167 | 126377 | 14558 | 14576 | 15112 |
| G | 27719 | 30032 | 31295 | 34199 | 34145 | 35013 | 72093 | 69541 | 67223 | 7543 | 7849 | 8010 |
| H | 14749 | 15086 | 14425 | 18443 | 17460 | 17910 | 34486 | 33937 | 36621 | 3913 | 3762 | 3690 |

Performance of the five GLP-1 antibodies and the parental wild type antibody are shown in Table 6. Apparent concentrations and real concentrations were calculated from the standard curves on the GLP-1 spot and anti-IgG spot, respectively. Based on the ratio of apparent concentrations over real concentrations, it was determined that four out of five mutants performed better than the parental wild type clone. The calculation was consistent over the dilution range of the samples (250 fold to 2,000 fold dilution).

TABLE 6

| | GLP-1 | | anti-IgG | | Performance |
|---|---|---|---|---|---|
| | Mean Signal | Apparent Conc. | Mean Signal | Real Conc. | adjust to wild type |
| Mutant 1 1000× diluted | 9855 | 2.94 | 32539 | 9.40 | 1.3 |
| Mutant 1 2000× diluted | 5175 | 1.42 | 16535 | 4.56 | 1.3 |
| Mutant 1 250× diluted | 33191 | 11.29 | 119525 | 38.76 | 1.2 |
| Mutant 1 500× diluted | 18205 | 5.81 | 63218 | 19.28 | 1.3 |
| Mutant 2 1000× diluted | 29720 | 9.99 | 34615 | 10.04 | 4.1 |
| Mutant 2 2000× diluted | 15120 | 4.73 | 17589 | 4.87 | 4.0 |
| Mutant 2 250× diluted | 107705 | 42.74 | 125432 | 40.88 | 4.4 |
| Mutant 2 500× diluted | 57815 | 20.98 | 66306 | 20.30 | 4.3 |
| Mutant 3 1000× diluted | 19007 | 6.09 | 24509 | 6.93 | 3.7 |
| Mutant 3 2000× diluted | 10012 | 2.99 | 12426 | 3.37 | 3.7 |
| Mutant 3 250× diluted | 65692 | 24.24 | 88905 | 27.97 | 3.6 |
| Mutant 3 500× diluted | 37401 | 12.89 | 47127 | 14.01 | 3.8 |
| Mutant 4 1000× diluted | 25822 | 8.55 | 29682 | 8.52 | 4.2 |
| Mutant 4 2000× diluted | 13274 | 4.09 | 14753 | 4.04 | 4.2 |
| Mutant 4 250× diluted | 83990 | 32.05 | 105550 | 33.78 | 4.0 |
| Mutant 4 500× diluted | 47480 | 16.82 | 57598 | 17.42 | 4.0 |
| Mutant 5 1000× diluted | 29827 | 10.03 | 34452 | 9.99 | 4.2 |
| Mutant 5 2000× diluted | 15548 | 4.88 | 17938 | 4.97 | 4.1 |
| Mutant 5 250× diluted | 97247 | 37.96 | 124984 | 40.72 | 3.9 |

TABLE 6-continued

| | GLP-1 | | anti-IgG | | Performance |
|---|---|---|---|---|---|
| | Mean Signal | Apparent Conc. | Mean Signal | Real Conc. | adjust to wild type |
| Mutant 5 500× diluted | 52840 | 18.96 | 65353 | 19.98 | 4.0 |
| Wild type 1000× diluted | 17255 | 5.47 | 69619 | 21.41 | 1.1 |
| Wild type 2000× diluted | 9006 | 2.66 | 35015 | 10.17 | 1.1 |
| Wild type 250× diluted | 56503 | 20.46 | 242344 | 85.72 | 1.0 |
| Wild type 500× diluted | 33092 | 11.25 | 130292 | 42.64 | 1.1 |

The normalization method described in this Example was used to successfully screen and rank antibodies in IgG format against the following antigens: TNFa human, IL-17A human, IL-21 human, IL-23p19 human, G-CSF human, Glucagon human, IL-17F human, MDC human, IFN-g human, IL-13 human, Eotaxin human, PYY human, C-peptide human, Ghrelin human and MIP1-a human.

The methods disclosed and claimed herein can be made and executed without undue experimentation considering the present disclosure. While the compositions and methods of this invention have been described in terms of embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All patents, patent applications, and publications are incorporated herein by reference in their entireties for all purposes.

What is claimed is:

1. A method of screening a candidate antigen-binding molecule for affinity to an antigen, comprising:
   a. contacting the candidate antigen-binding molecule with a substrate, the substrate comprising (i) an antigen immobilized on the substrate, and (ii) a normalization binding molecule immobilized on the substrate;
   b. detecting a binding of the candidate antigen-binding molecule to the antigen;
   c. detecting a binding of the candidate antigen-binding molecule to the normalization binding molecule to determine a concentration of the candidate antigen-binding molecule; and
   d. determining the affinity of the candidate antigen-binding molecule to the antigen from the binding of the candidate antigen molecule determined in (b) and the binding of the antigen-binding molecule to the normalization binding molecule determined in (c).

2. The method of claim 1, wherein the candidate antigen-binding molecule is selected from the group consisting of an antibody (Ab), an immunoglobulin G (IgG), an antigen-binding fragment (Fab), variable fragment (Fv), a single-chain fragment variable (scFv), an antibody with one V-gene domain, a bivalent diabody, and combinations thereof.

3. The method of claim 1, wherein the candidate antigen-binding molecule is displayed on a bacteriophage.

4. The method of claim 3, wherein the bacteriophage infects a bacterium selected from the group consisting of *Escherichia coli*, *Bacillus pumilus*, *Bacillus subtilis*, *Cellulosimicrobium cellulans*, *Oerskovia turbata*, *Pseudomonas aeruginosa*, *Pseudomonas syringae*, *Salmonella enterica* and *Thermus thermophilus*.

5. The method of claim 4, wherein the bacteriophage is an *E. coli* filamentous bacteriophage.

6. The method of claim 4, wherein the bacteriophage is selected from the group consisting of λ, M13, P1, T4, f1, fd and Mu.

7. The method of claim 1, wherein the substrate comprises a plurality of immobilized antigens.

8. The method of claim 7, wherein the substrate is a multi-well plate or a microparticle.

9. The method of claim 8, wherein the substrate is a multi-well plate and the immobilized antigen and the immobilized normalization binding molecule are located within one or more single wells of the multi-well plate; or
   wherein the substrate comprises a plurality of microparticles, wherein the microparticles are coded to discriminate between microparticles comprising the antigen and microparticles comprising the normalization binding molecule.

10. The method of claim 1, wherein the antigen and normalization binding molecule are immobilized on the substrate surface via at least one linker molecule.

11. The method of claim 10, wherein the at least one linker molecule is an oligonucleotide or wherein the at least one linker molecule is biotin complexed with streptavidin.

12. The method of claim 1, wherein the antigen and/or the normalization binding molecule is immobilized on the substrate surface via a targeting agent bound to the surface and a targeting agent complement indirectly bound to the antigen.

13. The method of claim 12, wherein the targeting agent complement is additionally bound to a linking agent, and the antigen is bound to a supplemental linking agent, wherein the linking agent and the supplemental linking agent are binding partners.

14. The method of claim 13, further comprising a bridging agent, wherein the bridging agent comprises: (i) a first binding site for the linking agent, and (ii) a second binding site for the supplemental linking agent.

15. The method of claim 1, wherein the normalization binding molecule is an antibody or antigen binding fragment thereof that binds an epitope on the candidate antigen-binding molecule.

16. The method of claim 15, wherein the epitope on the candidate antigen-binding molecule is a constant domain or fragment thereof of an antibody heavy chain or an antibody light chain.

17. The method of claim 1, wherein the normalization binding molecule is an antibody or antigen-binding fragment that specifically binds a phage coat protein or a capsid-attached tag on a bacteriophage.

18. The method of claim 17, wherein the phage coat protein is pIII, pVIII, pVII, pIX, or a fusion protein.

19. The method of claim 17, wherein the tag is Strep II tag (STAG), FLAG-tag and His-tag.

20. The method of claim 1, wherein the detecting of (b) and/or the detecting of (c) comprises measuring optical absorbance, fluorescence, phosphorescence, chemiluminescence, electrochemiluminescence, light scattering, magnetism, or a combination thereof.

21. A method of screening a candidate antigen-binding molecule for affinity to an antigen, comprising:

a. contacting (1) a control compound at a plurality of concentrations, and (2) a candidate antigen-binding molecule with a substrate, the substrate comprising (i) an antigen immobilized on the substrate, and (ii) a normalization binding molecule immobilized on the substrate;
b. detecting a binding of the candidate antigen-binding molecule to the antigen;
c. detecting a binding of the candidate antigen-binding molecule to the normalization binding molecule;
d. detecting a binding of the control compound at the plurality of concentrations to the normalization binding molecule, wherein the detecting produces a plurality of detection signals;
e. generating a standard calibration curve utilizing the plurality of detection signals;
f. determining a first and a second concentration for each candidate antigen-binding molecule, wherein the first concentration is an apparent concentration determined from the binding of the antigen-binding molecule to the antigen of (b), and the second concentration is an actual concentration determined from the binding of the antigen-binding molecule to the normalization binding molecule of (c), wherein the actual concentration of the candidate antigen-binding molecule binding is determined using the calibration curve; and
g. calculating a ratio of the first and second concentrations for candidate antigen-binding molecule, wherein the ratio is a relative affinity of the antigen-binding molecule to the antigen.

22. The method of claim 21, wherein the control compound is a bacteriophage, and the candidate antigen-binding molecule is displayed on a bacteriophage.

23. The method of claim 21, wherein the control is an antibody, and the candidate antigen-binding molecule is a mutated antibody.

* * * * *